United States Patent
Willner et al.

(10) Patent No.: US 11,602,460 B2
(45) Date of Patent: Mar. 14, 2023

(54) EUSTACHIAN TUBE DRUG ELUTING STENT

(71) Applicants: Ayal Willner, Long Beach, CA (US); Nina Sarah Yoshpe Maginot, Long Beach, CA (US); Namrata Varma, Long Beach, CA (US)

(72) Inventors: Ayal Willner, Long Beach, CA (US); Nina Sarah Yoshpe Maginot, Long Beach, CA (US); Namrata Varma, Long Beach, CA (US)

( * ) Notice: Subject to any disclaimer, the term of this patent is extended or adjusted under 35 U.S.C. 154(b) by 44 days.

(21) Appl. No.: 17/122,223

(22) Filed: Dec. 15, 2020

(65) Prior Publication Data
US 2022/0183891 A1    Jun. 16, 2022

(51) Int. Cl.
*A61F 11/20* (2022.01)
*A61F 2/844* (2013.01)
*A61F 2/82* (2013.01)

(52) U.S. Cl.
CPC ............ *A61F 11/202* (2022.01); *A61F 2/844* (2013.01); *A61F 2002/825* (2013.01); *A61F 2250/0067* (2013.01)

(58) Field of Classification Search
CPC .. A61F 2/848; A61F 2002/825; A61F 11/202; A61F 2/844; A61F 2250/0067
See application file for complete search history.

(56) References Cited

U.S. PATENT DOCUMENTS

| | | |
|---|---|---|
| 6,589,286 B1 | 7/2003 | Litner |
| 7,771,446 B2 | 8/2010 | Rutter |
| 2009/0043376 A1* | 2/2009 | Hamer et al. ............. A61F 2/06 623/1.2 |
| 2012/0046739 A1* | 2/2012 | von Oepen ............. A61F 2/915 623/2.11 |
| 2012/0136294 A1 | 5/2012 | Gonzales |
| 2015/0202089 A1* | 7/2015 | Campbell ............... A61B 1/227 600/478 |

FOREIGN PATENT DOCUMENTS

WO    2017035485 A1    3/2017

OTHER PUBLICATIONS

Park, Jung-Hoon, et al., "Transnasal Placement of a Balloon-Expandable Metallic Stent: Human Cadaver Study of the Eustachian Tube", J Vasc Interv Radiol 2018; 29:1187-1193.

* cited by examiner

*Primary Examiner* — Thomas McEvoy
(74) *Attorney, Agent, or Firm* — LeonardPatel PC; Sheetal S. Patel; Michael A. Leonard, II

(57) ABSTRACT

An eustachian tube (ET) drug eluting stent includes a plurality of longitudinal spars with spring-like elements between each of the plurality of longitudinal spars, creating smooth arcs between each of the plurality of longitudinal spars while minimizing impediment of mucociliary flow. The combination of the plurality of longitudinal spars with spring-like elements are configured to enter into the ET uncompressed.

7 Claims, 9 Drawing Sheets

EUSTACHIAN TUBE DRUG ELUTING STENT

FIELD

The present invention relates to a stent, and more particularly, to a drug eluting absorbable stent for the eustachian tube.

BACKGROUND

Eustachian tube dysfunction (ETD) is a condition where the eustachian tube (ET) is unable to completely aerate the middle ear space. This results in negative pressure within the middle ear cavity as air within that cavity is absorbed into the bloodstream. In turn, this leads to more collapse of the ET and worsening functioning in a vicious circle type of scenario. The end result can be fluid and infection requiring treatment. In children, fluid and infection are common, whereas in adults, a feeling of plugging or discomfort are the main manifestations. Microscopically, chronic inflammation of the ET mucosa is the hallmark of patients with ETD. In such cases, such sensations of plugging or discomfort may be due to this inflammation while actual function of the ET may be normal when measured by tympanometry.

Treatment of ETD

Treatment of ETD can be grouped into medical and surgical therapies. Medical therapies include antibiotics, oral steroids, intranasal steroids, decongestants, and allergy medications. Additional treatments include inducing the Valsalva maneuver, blowing against a resistance such as a balloon, or holding the nose and blowing. These treatments and maneuvers are used to either resolve the inflammation and allow return of normal ET function and resolution of the inflammation induced discomfort, or to overcome the blockage of the eustachian tube and re aerate the middle ear, or both.

Surgical treatment primarily consists of Pressure Equalizing tubes (PET). These tubes are placed surgically and straddle the tympanic membrane (TM). The tubes are generally extruded by the body in weeks to years, depending on the choice of PET. Specialized PETs, such as the Silverstein tube, are placed through an opening created in the scutum, the superior/medial part of the ear canal. These tubes, however, require a much larger surgical procedure. Finally, tympanomastoidectomy has been employed in the treatment of chronic ETD and its sequelae.

More recently, dilatation of the Eustachian Tube Orifice (ETO) has been evaluated in the treatment of chronic ETD. Balloons have been developed which both temporarily expand the cartilaginous ET and which seem to effect change in the lining of the ET by causing sloughing of the inflamed ET lining or mucosa. This leads to a rejuvenation of the mucosal layer, resulting in an ET lining with decreased inflammation and swelling, thus resulting in resolution of the ETD. These balloons are an adaptation of cardiac balloons used in angioplasty, which were adapted for use in the sinuses and then for use in the ET. They are elongated and oval in shape.

Stenting in the Aerodigestive Tract

Intersect™ is a company that makes sinus stents, and more specifically, produces mometasone eluting stents for the ethmoid cavity, the frontal recess, and the maxillary antrostomy. These stents release mometasone either for 2 weeks or for 3 months. They also either disintegrate in about 2-4 weeks after releasing mometasone for 2 weeks or partially disintegrate and are removed in about 3 months for those stents that elute mometasone for 3 months.

Stenting of the Eustachian Tube

Stenting of the eustachian tube has been examined. Some studies have looked at non-dissoluble stents, while others have looked at dissoluble stents. Dissoluble stents come in several types. For example, one type is inserted via lifting up the TM and placing the stent through the middle ear space into the bony, or middle ear side, of the eustachian tube. Another type acts as a "cap" on the nasopharyngeal end of the ET, with a small hole to allow fluid to come through from the middle ear into the nasopharynx. Yet another one is cylindrical in shape, and essentially covers the lining of the ET. These dissoluble stents have positive attributes, in that they are dissolvable and release medications.

However, the stents that have been described above have multiple short-comings. For instance, the stent that is inserted through the tympanostomy approach requires a significant surgical procedure to be placed and cannot be easily removed if not tolerated by the patient. The "cap" leaves only a small hole for the egress of the mucociliary blanket secretions normally produced by the mucosa of the ear and which serve to keep the ear healthy, and does not provide for drug delivery higher up in the ET.

Other stents, which do not follow the conical shape of the ET, lead to a mismatch in the fit and fail to maximize the drug delivery. All stents, but one, fail to consider the effect of the natural beat direction of the cilia, from the middle ear to the nasopharyngeal opening of the ET, which works to extrude the implant. The one stent that does have a mechanism to avoid extrusion is cylindrical rather than conical, and is solid, covering the entire mucosa. This stent again impedes the mucociliary flow, which is essential to the normal function and health of the ear.

Accordingly, an improved system comprising an improved ET balloon, an absorbable stent, which may or may not elute drugs, and an insertion device for this stent may be beneficial.

SUMMARY

Certain embodiments of the present invention may provide solutions to the problems and needs in the art that have not yet been fully identified, appreciated, or solved by current ET stents technologies. For example, some embodiments of the present invention pertain to an absorbable stent.

In an embodiment, an eustachian tube (ET) drug eluting stent includes a plurality of longitudinal spars with spring-like elements between each of the plurality of longitudinal spars. This configuration creates smooth arcs between each of the plurality of longitudinal spars while minimizing impediment of mucociliary flow. Further, the combination of the plurality of longitudinal spars with spring-like elements are configured to enter into the ET uncompressed.

BRIEF DESCRIPTION OF THE DRAWINGS

In order that the advantages of certain embodiments of the invention will be readily understood, a more particular description of the invention briefly described above will be rendered by reference to specific embodiments that are illustrated in the appended drawings. While it should be understood that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE EMBODIMENTS

Some embodiments generally pertain to an ET drug eluting stent that includes a plurality of longitudinal spars with spring-like elements between each of the plurality of longitudinal spars. This configuration creates smooth arcs between each of the plurality of longitudinal spars while minimizing impediment of mucociliary flow. Further, unlike convention ET drug eluting stents, the combination of the plurality of longitudinal spars with spring-like elements are configured to enter into the ET uncompressed.

Figure 1A:
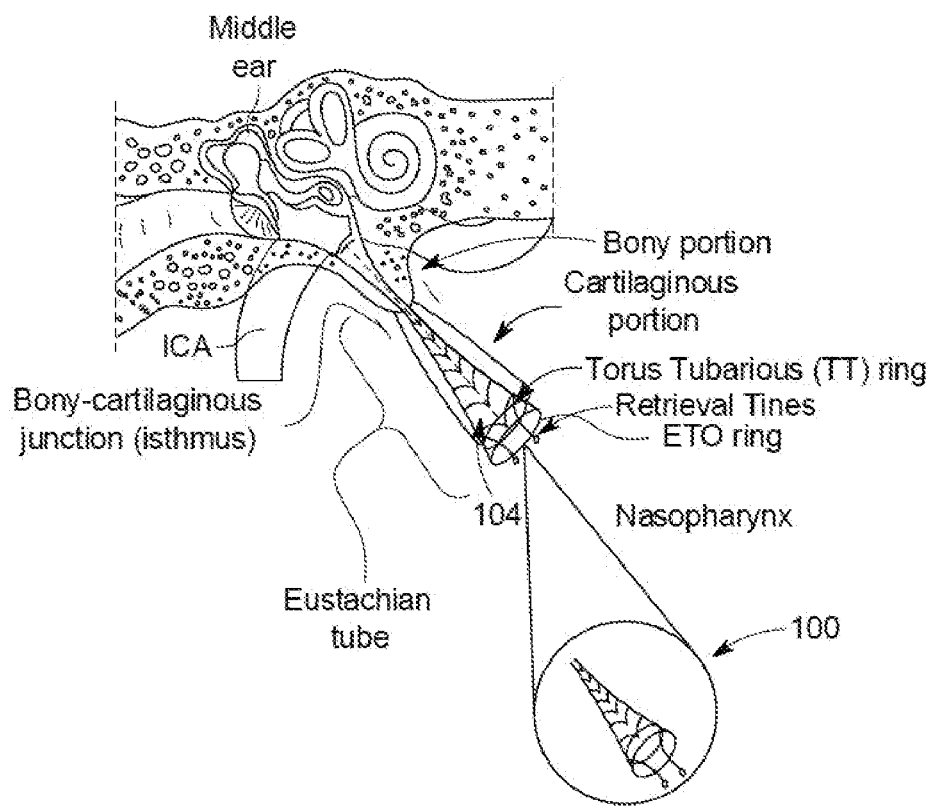
FIG. 1A is a diagram illustrating a middle ear with an absorbable stent 100 inserted therein, according to an embodiment of the present invention.

FIG. 1A is a diagram illustrating a middle ear with an absorbable stent 100 inserted therein, according to an embodiment of the present invention.

Stent

Figure 1B:
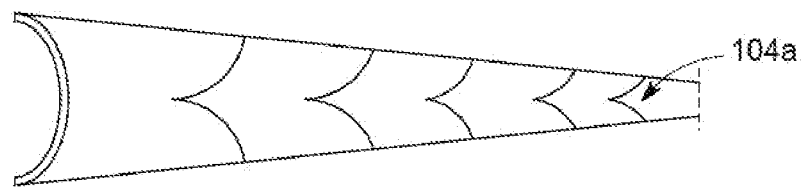
FIGS. 1B and 1C is a diagram illustrating a side view of stent, according to an embodiment of the present invention.
Figure 1C:
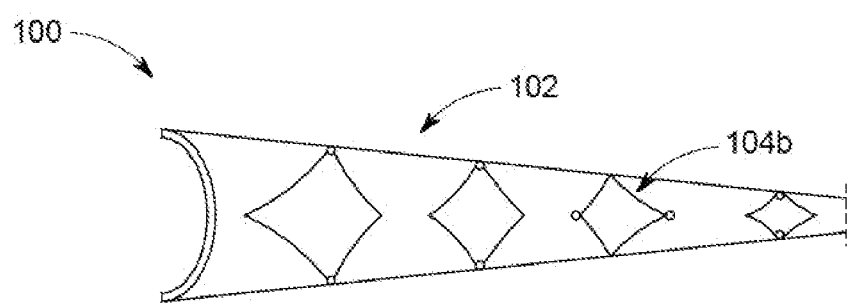

In some embodiments, stent 100 includes longitudinal spars 102 that are connected by 'Y' shaped elements 104a or 'diamond' shaped elements 104b, both of which form a structure that is arranged in a conical fashion. FIGS. 1B and 1C are diagrams illustrating a side view of stent 100, according to an embodiment of the present invention. As shown in FIG. 1B, 'Y' shaped elements 104a, for example, act as a spring and are capable of decompressing when the base of the 'Y' shaped elements move as longitudinal spar 102 compress. Similarly, as shown in FIG. 1C, 'diamond' shaped elements 104b may perform a similar function as 'Y' shaped elements 104a.

It should be noted that most stents are designed to go into the nose compressed radially, and are then released from the introducer to expand toward their pre-compression state. Given the size of stent 100, some embodiments allow stent 100 to be placed through the nose in an uncompressed manner and placed into the ET. As stent 100 travels into the ET, stent 100 begins to compress. Once stent 100 is placed far enough inside of the ET so that the retaining hooks are engaged inside of the ET, the plunger pushes the stent off of the introducer. See retaining hooks 206 of FIG. 2 as an example. The introducer may then push away from stent 100 and back towards the nose for removal. See conceptual flow diagram in FIG. 5 and the diagram in FIG. 6, which is described in more detail below.

Conceptually, this is like taking a cone that is just a little larger than another cone and placing the bigger cone into the smaller one. The larger cone in this example is circumferentially compressed rather than being radially compressed. This is another way in which stent 100 is different from other commercially available stents. This circumferential compression is achieved by the "Y" shaped or "diamond" shaped elements (or springs) 104a, 104b, both of which allow for compression and are themselves curved to be part of the conical shape. Furthermore, the introducer prevents radial collapse of stent 100 as it is being inserted in the ET.

Depending on the embodiment, stent 100 is circumferentially compressible to facilitate insertion. In some additional embodiments, stent 100 is placed into the ET, either before or after dilatation with a ET dilation balloon. Stent 100 is also composed of material configured to disintegrate beginning two (2) weeks to two (2) months after insertion, and to secrete medication for up to two (2) months after insertion. In some embodiments, stent 100 may be composed of polylactic-co-glycolic acid, which is known for its biodegradability.

The size of stent 100 is predetermined via normative values of adults and children. It is placed into the ET close to, but not at, the isthmus of the ET, where the cartilage is transitioned to bone. This allows for the drug to diffuse to the isthmus without stent 100 blocking the narrowest part of the ET.

Although not shown in FIG. 1, retaining hooks (or barbs) are introduced as a way to maintain stent 100 in situ, while an open format with struts as opposed to solid walls allows for maximization of mucociliary flow. See, for example, FIG. 2 for a more detailed description of retaining hooks 206. The conical design to follow the shape of the ET is introduced. It should be appreciated the drug (or medication) may be held within nanoparticles that dissolve and the particles are held in a hydrogel that forms stent 100.

Figure 2A:
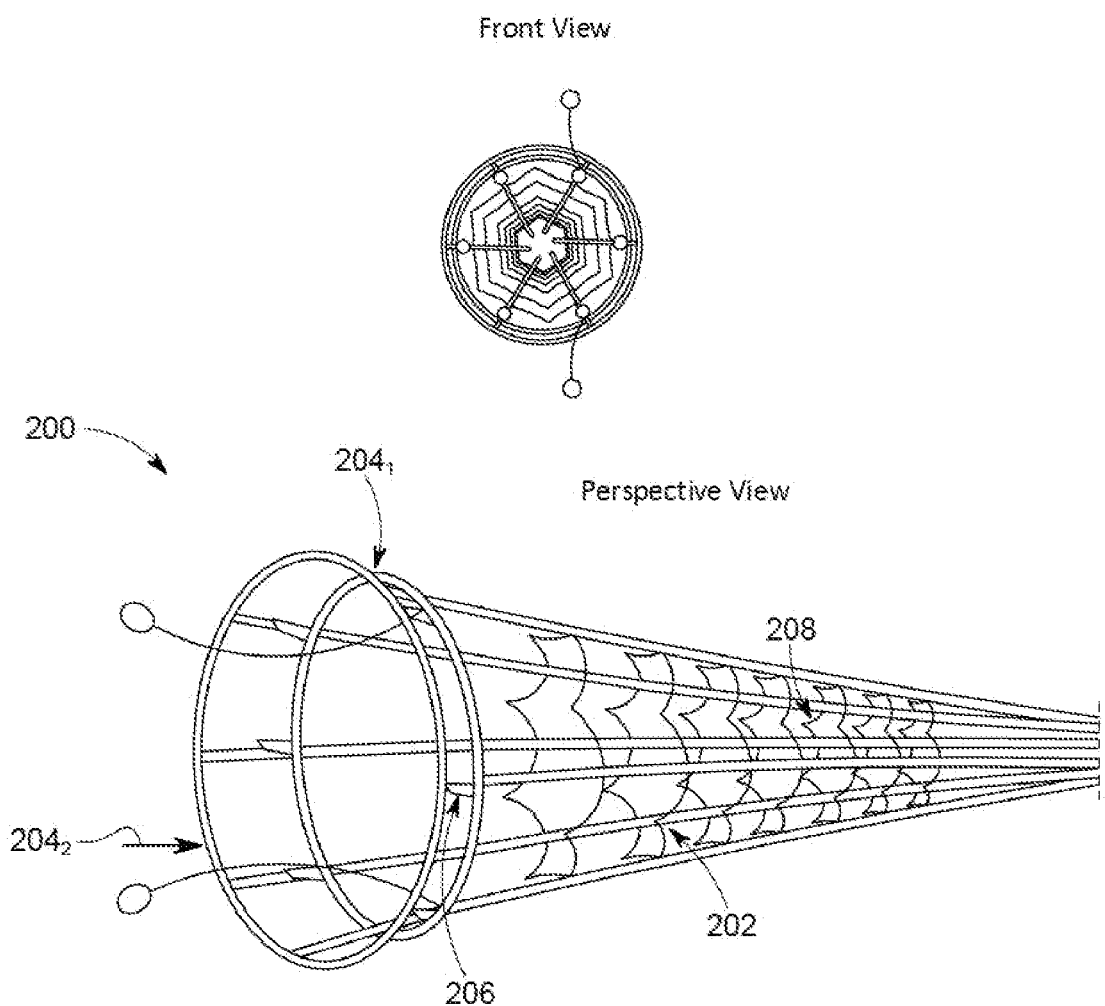
FIG. 2A is a diagram illustrating an absorbable stent for the ET, according to an embodiment of the present invention.
Figure 2B:
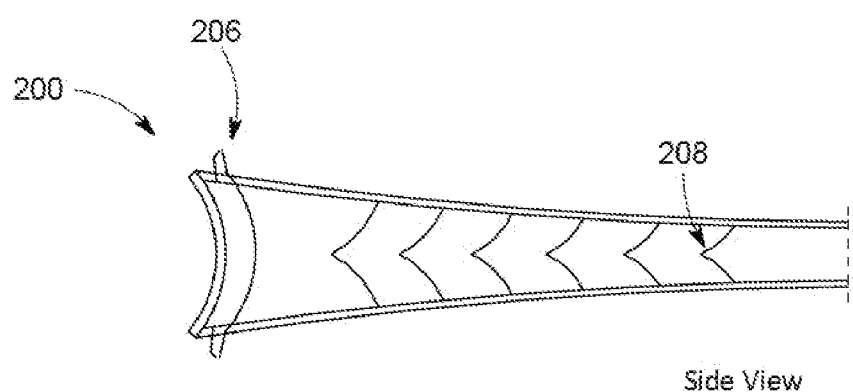
FIG. 2B is a diagram illustrating a side view of the absorbable stent, according to an embodiment of the present invention.
Figure 2C:
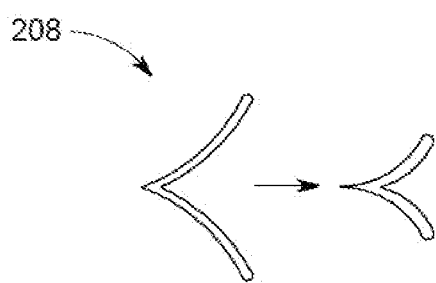
FIG. 2C is a diagram illustrating the compressive nature of compression springs, according to an embodiment of the present invention.

FIGS. 2A and 2B are diagrams illustrating an absorbable stent 200 for the ET, according to an embodiment of the present invention. In this embodiment, stent 200 includes a plurality of longitudinal spars 202. In one example, there may be six (6) longitudinal spars. However, the number of longitudinal spars may depend on a number of factors. For example, there may be a N number of longitudinal spars to give sufficient support and fit with a conical shape with the 'Y' shaped or 'Diamond' shaped elements, creating smooth arcs between the spars, while minimizing the impediment of mucociliary flow.

Stent 200 may also include two (2) complete rings (a first ring $204_1$ and a second ring $204_2$) around longitudinal spars 202. First ring $204_1$ may be approximately 4 mm in diameter and a second ring $204_2$ may be approximately 7 mm. The smaller first (inner) ring $204_1$ is the one with barbs 206. Barbs (or retaining hooks) 206 and medial (first and second) rings $204_1$ and $204_2$. In this embodiment, ring $204_2$ is most medial and sits just internal to the torus tubarious (TT) while ring $204_1$, which comprises barbs 206, sits just inside of the ET itself. Ring $204_2$ can be thicker, and may be used to grasp the stent for removal when necessary.

Between longitudinal spars 202 are compression springs (spring-like elements) 208. See, for example, FIG. 2B, which is a diagram illustrating a side view of absorbable stent 200, according to an embodiment of the present invention. Compression springs 208 hold longitudinal spars 202 in position and allow for the compression of stent 200. Compression springs 208 also follow the curve of the periphery of stent 200. Compression springs 208 are designed to follow the curve of the periphery of the conical shape of stent 200. This allows for contact of the periphery of stent 200 with the wall of the ET, making a "circle" with the longitudinal spars 202. Each compression spring 208 may be compressed independently allowing stent 200 to maintain contact with the luminal mucosal surface of the ET. This allows for the diffusion of the drug from stent 200 to the luminal mucosa of the ET.

Compression springs 208 may allow for the maintenance of the length of stent 200, as well as the longitudinal relationships between longitudinal spars 202. In other words, as compression springs 208 compress, longitudinal spars 202 move closer to each other along the arc of the circumference of stent 200. However, longitudinal spars 202 do not move longitudinally in relationship to one another, i.e., sliding past one another. In conventional stents, the configurations of the stent are longer when compressed than when open. As they expand, the forward edge moves "backward" or the back edge moves "forward". Such a configuration, within the ET, may lead to a malpositioning of the stent as it gets compressed.

Compression springs 208 may also allow for the ET to provide compressive force, which collapses compression springs 208. See, for example, FIG. 2C, which is a diagram illustrating the compressive nature of compression springs 208, according to an embodiment of the present invention. Unlike the current Propel™ stents, which use a wound-spring type action to cause the stents to "spring" open after being compressed, stent 200 uses a mechanism more akin to a "leaf-spring", which is used in the automotive suspension system. This is the portion of stent 200 that goes up or down and is compressed as two longitudinal spars 202 come closer to each other.

Also, unlike other stents, the ET provides the compressive force to compress stent 200 by compressing compression springs 208. Typically, when a nasal stent is pushed through the nose, the stent is introduced into the nose compressed, in a sleeve, and is then pushed out of the sleeve and expands radially and in this way may push the ethmoid cavity out. In cardiac procedures, the stents are designed to go in compressed and expand the artery or support the artery. In this case, the idea is to keep the medication releasing device in contact with the mucosal surface. So, as stent 200 goes into the ET after passing through the nose, the ET gently compresses stent 200 and maintains contact with stent 200.

Depending on the embodiment, stent 200 may be used in conjunction with ETO dilation. See a more detailed description of the balloon apparatus below.

Insertion of the Stent

Figure 3:
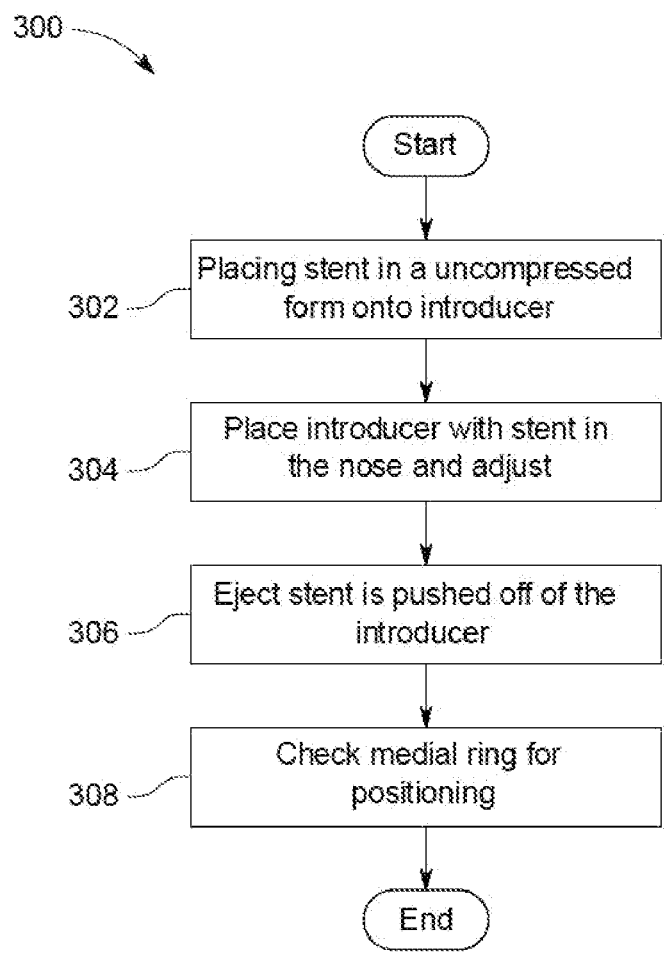
FIG. 3 is a flow diagram illustrating a method for inserting the stent of FIG. 1 or 2, according to an embodiment of the present invention.

FIG. 3 is a flow diagram illustrating a method 300 for inserting the stent of FIG. 1 or 2, according to an embodiment of the present invention. In some embodiments, method 300 begins at 302 with preparing and placing the stent in an uncompressed form onto an introducer. At 304, the introducer is placed in the nose and adjusted such that the tip enters the ET and follows it up to where it is too wide to continue. At 306, the stent is then pushed off of the introducer, and the introducer is withdrawn from the nose. At 308, the medial ring is checked for positioning, snugly along the internal aspect of the TT.

Balloon

Figure 4:
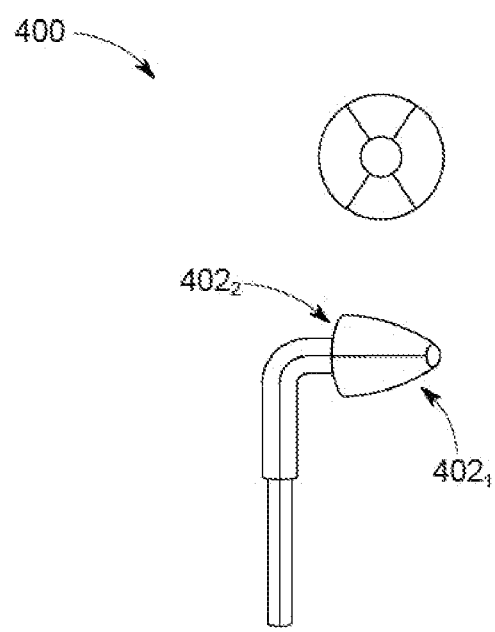
FIG. 4 is a diagram illustrating a balloon for the ET, according to an embodiment of the present invention.

FIG. 4 is a diagram illustrating a balloon 400 for the ET, according to an embodiment of the present invention. While the idea of balloon placement, via an introducer, with a "stop" to prevent placement of the balloon through the ET isthmus has been developed, some embodiments introduce a novel shape to balloon 400. Current balloons for placement into the ET are in the shape of an oval, which were adapted from cardiac angioplasty balloons. Other modifications of the balloon have been made for use in the airway. These balloons, however, are wider at each end preventing movement of the balloon during inflation.

Some embodiments generally pertain to a conically shaped balloon 400. This conically shaped balloon 400 follows the shape of the ET rather than the generic oval shaped balloons. This novel shape of balloon 400 allows for more uniform dilatation of the ET via more uniform pressures on the mucosa.

As an example, placing an oval shaped balloon into a conical funnel allows a small part of the balloon to contact the wall of the funnel. In currently available balloon configurations for nasal and ET use, the balloons are constructed to achieve a certain shape as saline is used to fill the balloon. Once this shape is reached, further inflation leads to increase in pressure, not continued expansion of the balloon. Therefore, no matter how much pressure the oval balloon develops, the balloon only contacts a small amount of the above mentioned funnel. Alternatively, if the balloon in this example is shaped like the funnel itself, the balloon exerts pressure on the walls of the funnel in a much more uniform fashion.

While the ET, which is elastic in nature, does contact the balloon over a larger surface area than a firm conical funnel, it may still be stretched and compressed in an uneven fashion. A conical balloon will better evenly distribute the pressure produced inside the balloon.

In some embodiments, the diameter of first location $402_1$ is smaller (e.g., approximately 2 mm) and the diameter of second location $402_2$ is larger (e.g., 6 to 7 mm). This difference is different in diameters allow balloon 400 to be shaped conically.

Insertion of the Balloon

Figure 5:
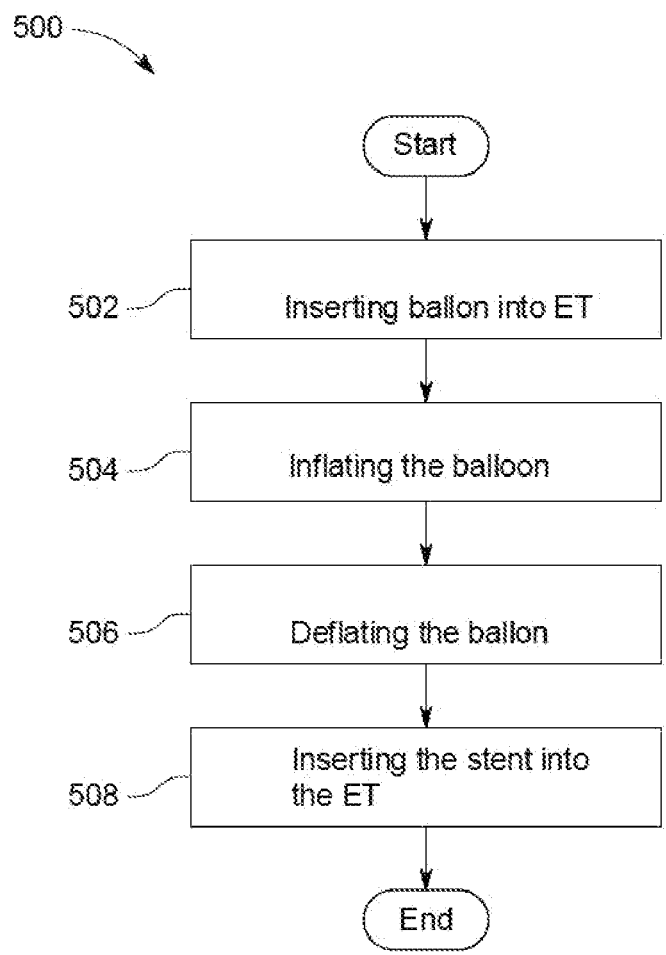
FIG. 5 is a flow diagram illustrating a method for inserting a balloon of FIG. 4 into the ET prior to inserting the stent of FIG. 1 or 2, according to an embodiment of the present invention.

FIG. 5 is a flow diagram illustrating a method 500 for inserting a balloon of FIG. 4 into the ET prior to inserting the stent of FIG. 1 or 2, according to an embodiment of the present invention. In some embodiments, method 500 begins at 502 with inserting the conical shaped balloon into the ET. At 504, the conical shaped balloon is inflated with an inflation device. At 506, after a predetermined time (e.g., 1 to 2 minutes) has elapsed, the conical shaped balloon is deflated, and the balloon is removed. At 508, after removal of the balloon, the stent is inserted into the ET using an introducer. See the description of the stent insertion with respect FIG. 3 above or FIG. 6 below.

Figure 6:
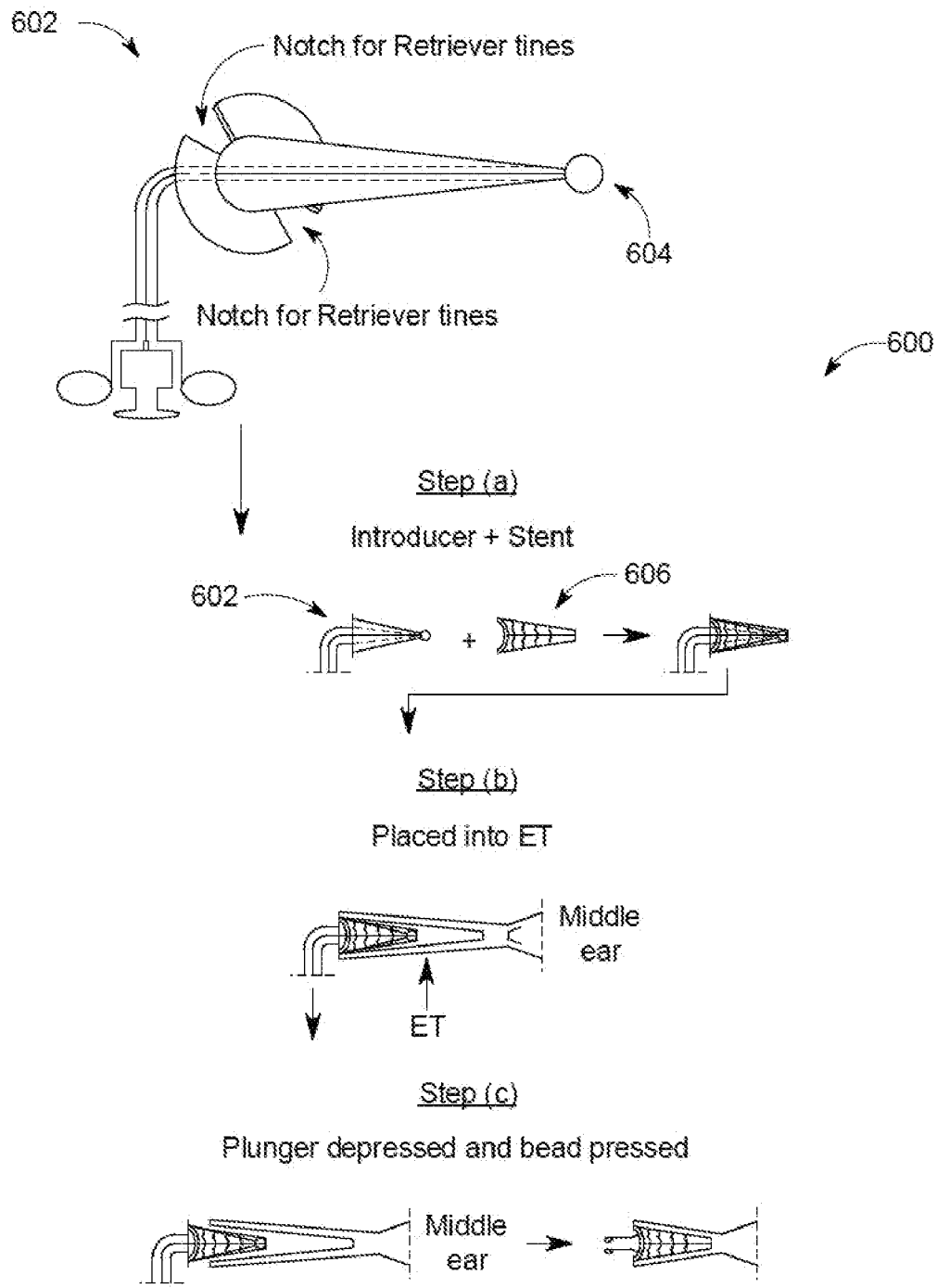
FIG. 6 is a diagram illustrating a flow for inserting the stent into the ET, according to an embodiment of the present invention.

FIG. 6 is a diagram illustrating a flow 600 for inserting the stent into the ET, according to an embodiment of the present invention. In some embodiments, at step (a), an introducer 602 is placed within stent 606. Unlike conventional insertion devices, introducer 602 is placed inside of stent 606 to provide support and prevent stent 606 from folding inward when stent 606 is being compressed during insertion into the ET. At step (b), stent 606 attached to introducer 602 is placed inside of, or inserted into, the ET. At step (c), a plunger 604 on introducer 602 is pressed, releasing stent 604 into the ET. In some embodiments, introducer 602 pushes stent 606 into the ET when stent 606 is being released from introducer 602. This is in contrast to current stents that are placed in a "sleeve", which is placed into position and ejected from the sleeve, and then springing open and expanding.

Some embodiments include two notches in introducer 602, each on opposite sides of introducer 602, as illustrated in FIG. 6, and allow for a space for stent 606 which has extra retrieval tines to remove stent 606. Although not shown in the figures, alternative embodiments do not include a notch with the most medial ring being used to remove the stent.

Figure 7:
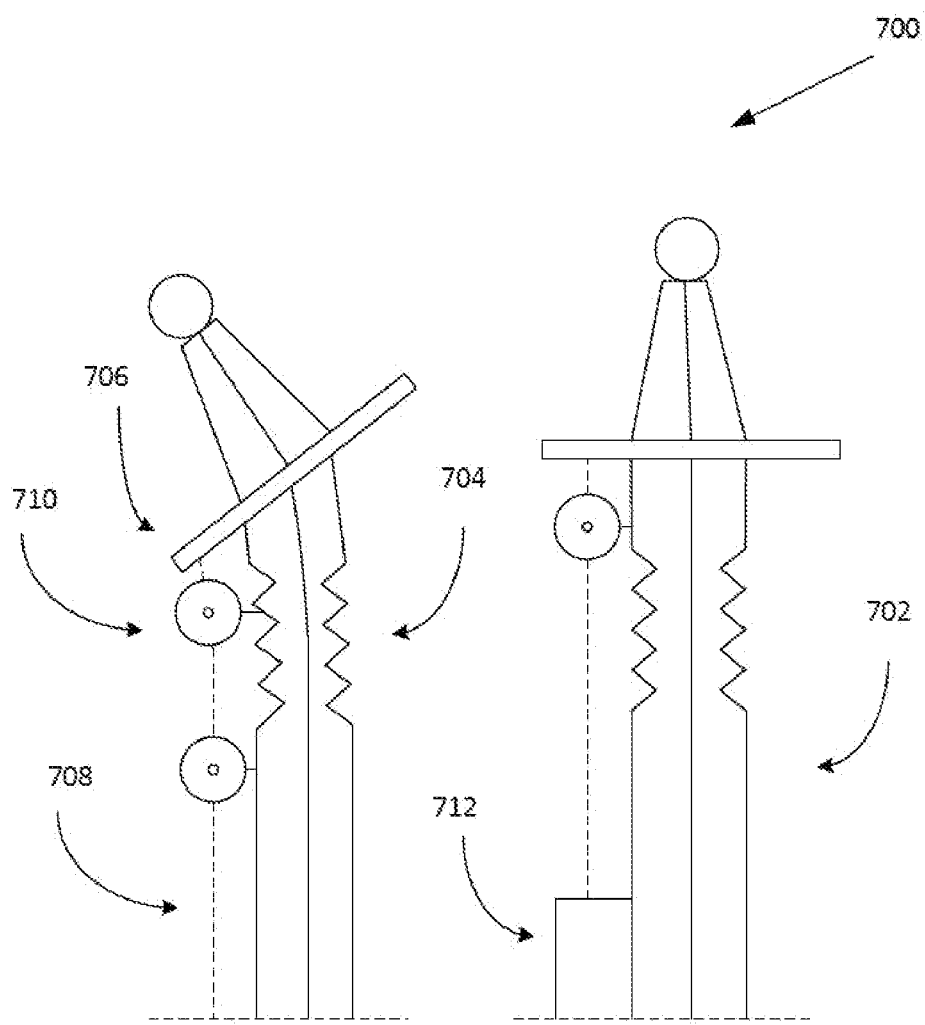
FIG. 7 is a diagram illustrating an introducer, according to an embodiment of the present invention.

FIG. 7 is a diagram illustrating an introducer 700, according to an embodiment of the present invention. In some embodiments, introducer 700 may be used for introducing an ET drug eluting stent inside of an ET. Introducer 700 may include an elongated shaft 702 configured to be inserted inside of the ET drug eluting stent. Elongated shaft 702 with the ET drug eluting stent being placed around the elongated shaft is configured to conform or bend when inserted inside of, and traversing into, an ET. Also, in some embodiments, a portion of elongated shaft 702 is composed of an accordion-like spring 704 allowing elongated shaft 704 to bend when being inserted into the ET.

Introducer 700 may also include a plunger 706 configured to pull on a string 708 when pushed. String 708 is configured to run parallel to elongated shaft 702. Further, string 708, when plunger 706 is pressed, is configured to force elongated shaft 702 to bend, turning elongated shaft 702 towards the ET.

Also, in some embodiments, elongated shaft 702 includes one or more steering loop 710 extended out from elongated shaft 702. One or more steering loops 710 are configured to guide string 708 along a side of elongated shaft 702, enabling a head of introducer 700 to bend towards the ET. At end of elongated shaft 702 is a guide mechanism 712 for string 708.

It should be noted that introducer 700 with the attached stent is introduced with the stent pointing straight in the direction of shaft 702 of introducer 700. After passing the posterior aspect of the inferior turbinate (i.e., "clearing" the turbinate), shaft 702 bends up to 70 degrees to the side of string 708, in some embodiments. String 708 is a filamentous structure that is used to pull the platform of the insertion tool, on which sits the stent, to the 70 degree angle. This allows the stent to be aligned with the ETO for appropriate insertion, once it has cleared the turbinate. All of this is accomplished by depressing the plunger which in turn pulls on "string" 708, which in turn pulls the platform on which the stent sits to the side. This is accomplished by having a section, distally, of the insertion tool, that can be bent by virtue of its "accordion" like construction, which allows for bending of the insertion too distally, similar to the way a bendable straw bends. The platform can passively unbend as it is withdrawn from the ET, reloaded, flipped over, and the mirror procedure completed on the other side.

It will be readily understood that the components of various embodiments of the present invention, as generally described and illustrated in the figures herein, may be arranged and designed in a wide variety of different configurations. Thus, the detailed description of the embodiments of the present invention, as represented in the attached figures, is not intended to limit the scope of the invention as claimed, but is merely representative of selected embodiments of the invention.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

One having ordinary skill in the art will readily understand that the invention as discussed above may be practiced with steps in a different order, and/or with hardware elements in configurations which are different than those which are disclosed. Therefore, although the invention has been described based upon these preferred embodiments, it would be apparent to those of skill in the art that certain modifications, variations, and alternative constructions would be apparent, while remaining within the spirit and scope of the invention. In order to determine the metes and bounds of the invention, therefore, reference should be made to the appended claims.

The invention claimed is:

1. A eustachian tube (ET) drug eluting stent, comprising:
    a plurality of longitudinal spars with a plurality of spring-like elements between each of the plurality of longitudinal spars, creating smooth arcs between each of the plurality of longitudinal spars while minimizing impediment of mucociliary flow, wherein
    the combination of the plurality of longitudinal spars with spring-like elements are configured to enter into the ET uncompressed; and
    a proximal end of the ET drug eluting stent, wherein the proximal end of the ET drug eluting stent remains in an uncompressed, with a fully expanded radial diameter without undergoing significant change in the radial diameter when inserted into the ET, wherein
    the ET drug eluting stent
        has measurements that approximate those of the ET in relation to length and diameter and is tapered from the proximal end to a distal end, thereby extending from outside of the ET to approximately the isthmus,
        is appositional to mucosa of approximately the entire length and area of a cartilaginous area of the ET, and
        has a radially uncompressed distal diameter significantly similar to the diameter of a human ET isthmus, and
    the plurality of longitudinal spars compress together around the circumferential arc of the ET without forming a bundle of longitudinal spars and without blocking the ET, thereby remaining appositional to the mucosa and maintaining patency and functionality of the ET.

2. The ET drug eluting stent of claim 1, wherein the spring-like elements are configured to hold each of the plurality of longitudinal spars in position and allow for the compression of the ET drug eluting stent.

3. The ET drug eluting stent of claim 1, wherein the spring-like elements are configured to follow a curve of a periphery of a conical shape of the ET drug eluting stent.

4. The ET drug eluting stent of claim 1, wherein each of the spring-like elements are configured to compress independently from one another, allowing the ET drug eluting stent to maintain contact with a luminal surface of the ET.

5. The ET drug eluting stent of claim 1, wherein each of the spring-like elements are configured to compress each of the plurality of spars as the ET drug eluting stent is moved inside of the ET, wherein during the compression of each of the plurality of spars, the plurality of spars move closer to each other along an arc of a circumference of the ET drug eluting stent without moving longitudinally in relationship to one another.

6. The ET drug eluting stent of claim 1, further comprising:

a first ring and a second ring around each of the plurality of spars, the second ring being smaller than the first ring and placed internal to the first ring along the plurality of spars; and a plurality of retaining hooks along a circumference of the second ring, each of the retaining hooks configured to maintain position of the ET drug eluting stent within the ET.

7. The ET drug eluting stent of claim 1, further comprising:

a plurality of retrieval tines configured to assist in removal of the ET drug eluting stent when pulled by a user.

* * * * *